United States Patent [19]

Springer et al.

[11] Patent Number: 5,728,868
[45] Date of Patent: Mar. 17, 1998

[54] PRODRUGS OF PROTEIN TYROSINE KINASE INHIBITORS

[75] Inventors: Caroline Joy Springer, Sutton; Richard Marais, London, both of United Kingdom

[73] Assignee: Cancer Research Campaign Technology Limited, London, United Kingdom

[21] Appl. No.: 591,494

[22] PCT Filed: Jul. 15, 1994

[86] PCT No.: PCT/GB94/01532

§ 371 Date: Jul. 1, 1996

§ 102(e) Date: Jul. 1, 1996

[87] PCT Pub. No.: WO95/02420

PCT Pub. Date: Jan. 26, 1995

[30] Foreign Application Priority Data

Jul. 15, 1993 [GB] United Kingdom .............. 9314702
Jul. 15, 1993 [GB] United Kingdom .............. 9314703

[51] Int. Cl.$^6$ ............................................. C07C 275/00
[52] U.S. Cl. ..................... 562/439; 562/405; 560/34; 514/44; 424/93.6
[58] Field of Search ................. 424/93.6; 560/134, 560/135, 136, 137, 34; 514/414; 564/180; 562/439, 405

[56] References Cited

U.S. PATENT DOCUMENTS 5,405,990 4/1995 Burke et al. ................. 560/134

FOREIGN PATENT DOCUMENTS

WO 93/08288 4/1993 WIPO.

OTHER PUBLICATIONS

Bagshawe et al. (1994); Annals of Oncology 5:879–891.
Melton et al. (Oct. 8, 1996); J. Natl. Cancer Inst., 88 (3–4):153–65.
Deonarain et al. (1994); Brit. J. Cancer, 70 (5):786–94.
Springer et al. (1995); Anti-Cancer Drug Design, 10:361–372.
Bashawe (Oct. 8, 1996); Molecular Medicine: 425–431.
Saperstein et al. (1989); Biochemistry, 28:5694–5701.
Gazit et al. (1989); J. Med. Chem., 32:2344.
Orkin et al. (1995); Report on Gene Therapy By NIH.

Primary Examiner—Christopher S. F. Low
Assistant Examiner—Dave T. Nguyen
Attorney, Agent, or Firm—Spencer & Frank

[57] ABSTRACT

A compound which comprises a prodrug of a protein tyrosine kinase inhibitor (PTKi) linked to a protecting group which is capable of being cleaved from the compound to release the PTKi, said PTKi prodrugs including tyrphostins, of formula (I).

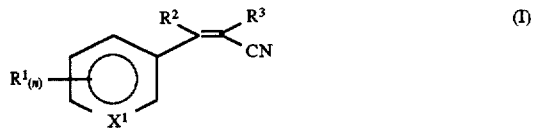

where X represents C, N or a group N→O, n is 1 to 3; each group $R^1$, which may be the same or different is H, OH, mercapto, carboxy, formyl, $C_{1-4}$ alkyl, $C_{2-4}$ alkenyl, $C_{1-4}$ alkoxy, $C_{1-4}$ alkylthio, carboxy$C_{1-4}$ alkyl, carboxy$C_{2-4}$ alkenyl, $C_{1-4}$ alkylsulphoxy, halo, nitro, amino, $C_{1-4}$ alkylamino, or $C_{1-4}$ dialkylamino, or when n is 2 or 3 two $R^1$ groups may together form a methylenedioxy or ethylenedioxy group; $R^2$ is H, OH, $C_{1-4}$ alkyl or together with position 2 of the ring to which the group(s) $R^1$ is (are) attached forms a 5 or 6 membered aliphatic or heterocyclic ring, optionally containing a ketone group; and $R^3$ is cyano, carboxy, carbamoyl, thiocarbamoyl, C(O)HNCH$_2$CN, C(NH$_2$)=C(CN$_2$), an alpha keto C(O)$R^4$ where $R^4$ is 3,4-dihydroxyphenyl or 2-thiophene or an alpha amido C(O)NHR$^5$ where $R^5$ is benzyl, phenyl, or 2,4-dimethoxyphenyl; provided that at least one of $R^1$ and $R^2$ is mercapto, hydroxy or amino.

3 Claims, No Drawings

PRODRUGS OF PROTEIN TYROSINE KINASE INHIBITORS

This application is a filing under 35 U.S.C. 371 of PCT/GB94/01532 filed 15 Jul. 1994.

FIELD OF THE INVENTION

The present invention relates to prodrugs and their use in the treatment of tumours.

TECHNOLOGY REVIEW

The use of prodrugs represents a clinically very valuable concept in cancer therapy since, particularly where the prodrug is to be converted to an anti-tumour agent under the influence of an enzyme that is linkable to a monoclonal antibody that will bind to a tumour associated antigen, the combination of such a prodrug with such an enzyme monoclonal/antibody conjugate represents a very powerful clinical agent. This approach to cancer therapy, often referred to as "antibody directed enzyme/prodrug therapy" (ADEPT) is disclosed in WO88/07378.

More recently, a similar approach ("VDEPT") has been proposed where in place of an antibody/enzyme conjugate, tumour cells are targeted with a viral vector carrying a gene encoding an enzyme capable of activating a prodrug. The gene may be transcriptionally regulated by tumour specific promoter or enhancer sequences. The viral vector enters tumour cells and expresses the enzyme, in order that a prodrug is converted to an active drug only in the vicinity of the tumour cells (Huber et al, Proc. Natl. Acad. Sci. USA (1991) 18, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French Anderson, Annu. Rev. Biochem., 1993, 62;191. The term "GDEPT" (gene-directed enzyme prodrug therapy) is used to include both vital and non-viral delivery systems.

Although the GDEPT and ADEPT systems enhance the concentrations of anti-tumour agents which may be delivered to the site of a tumour, there is still a need to enhance the specificity of drug delivery. In both systems, active drug can be released into the environment of normal cells and cause damage. In the case of ADEPT, this can be caused by activation of prodrug by conjugates which have failed to localise at the tumour site. In GDEPT, transformation of normal tissue may lead to residual levels of expression of the enzyme away from the tumour or active drug may be released from tumour cells. Although ways to increase the specificity of the ADEPT system is disclosed in WO89/10140, there remains a continuing need to improve the level of ADEPT and GDEPT specificity.

SUMMARY OF THE INVENTION

The present invention addresses such problems by the use of a novel class of prodrugs, which are prodrugs of protein tyrosine kinase (PTK) inhibitors. Some PTKs are known to be over-expressed by some types of tumours such as in breast and ovarian carcinomas, where the cErbB2 gene is over-expressed. Certain compounds have been found to be selective for PTKs and thus are relatively non toxic to cells which do not over-express PTKs.

The use of such compounds in ADEPT or GDEPT thus provides an increased level of specificity for the treatment of tumour cells. Prodrugs based upon PTK-inhibitors will be converted into PTK inhibitors primarily at the site of a tumour, but at the same time release of PTK-inhibitors at other sites or from the tumour will not cause cytotoxicity comparable to the release of non-specific cytotoxic drugs.

DETAILED DESCRIPTION OF THE INVENTION

In one aspect, the present invention provides a compound which comprises a prodrug of a protein tyrosine kinase inhibitor (PTKi) linked to at least one protecting group said group being capable of being cleaved from said compound to release the protein tyrosine kinase inhibitor or a physiologically acceptable derivative of said prodrug.

The prodrug is of the general formula:

PTKi-PRT where PTKi compound is a compound with PTK inhibitory activity and PRT is at least one protecting group capable of being cleaved from the PTK inhibitor by the action of an enzyme.

Suitable PTKs include tyrphostins. Tyrphostins are low molecular weight (e.g. less than 2,000) styryl containing inhibitors of protein tyrosine kinase which are capable of binding to the subsite of protein tyrosine kinase domains. Suitable tyrphostins include those described by Gazit et al (Gazit et al, J. Med. Chem. (1989) 32, 2344) and Gazit et al (J. Med. Chem. (1991) 43; 1896–1907) and especially tyrphostins of the general formula (I)

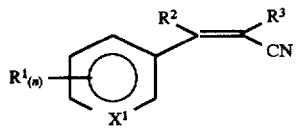

where X represents carbon, a nitrogen or a group N→O, n is an integer from 1 to 3;
each group $R^1$, which may be the same or different is hydrogen, hydroxy, mercapto, carboxy, formyl, $C_{1-4}$alkyl, $C_{2-4}$ alkenyl, $C_{1-4}$alkoxy, $C_{1-4}$alkylthio, carboxy$C_{1-4}$alkyl, carboxy$C_{2-4}$ alkenyl, $C_{1-4}$alkylsulphoxy, halo (ie. fluoro, chloro, bromo or iodo), nitro, amino, $C_{1-4}$alkylamino, or $C_{1-4}$dialkylamino, or when n is 2 or 3 two $R^1$ groups may together form a methylenedioxy or ethylenedioxy group;
$R^2$ is hydrogen, hydroxy, $C_{1-4}$alkyl or together with position 2 of the ring to which the group(s) $R^1$ is(are) attached forms a 5 or 6 membered aliphatic or heterocylic ring, said 5 or 6 membered ring optionally containing a ketone group; and $R^3$ is cyano, carboxy, carbamoyl, thiocarbamoyl, a group C(O) HNCH$_2$CN, a group C(NH$_2$)=C(CN)$_2$, an alpha keto group C(O)$R^4$ where $R^4$ is 3,4-dihydroxyphenyl or 2-thiophenyl or an alpha amido group C(O)NHR$^5$ where $R^5$ is benzyl, phenyl or 2,4-dimethoxyphenyl;
provided that at least one of the groups $R^1$ and $R^2$ is mercapto, hydroxy or amino.

In a preferred embodiment, X is C; n is an integer from 1 to 3; each group $R^1$, which may be the same or different is hydrogen, hydroxy, carboxy, formyl, $C_{1-4}$alkyl, $C_{2-4}$ alkenyl, $C_{1-4}$alkoxy, carboxy$C_{1-4}$alkyl, carboxy$C_{2-4}$ alkenyl, halo (ie. fluoro, chloro, bromo or iodo), nitro, amino, $C_{1-4}$alkylamino, or $C_{1-4}$dialkylamino, or when n is 2 or 3 two $R^1$ groups may together form a methylenedioxy or ethylenedioxy group; $R^2$ is hydrogen, hydroxy or $C_{1-4}$alkyl; and $R^3$ is cyano, carboxy, carbamoyl, thiocarbamoyl, a group C(O)HNCH$_2$CN or a group C(NH$_2$)=C(CN)$_2$.

Most preferably, X represents carbon, n is an integer from 1 to 3; each group $R^1$, which may be the same or different is hydrogen, hydroxy or amino; $R^2$ is hydrogen or hydroxy; and $R^3$ is cyano, a group $C(O)HNCH_2CN$, a group $C(NH_2)=C(CN)_2$, an alpha keto group $C(O)R^4$ where $R^4$ is 3,4-dihydroxyphenyl, or an alpha amido group $C(O)NHR^5$ where $R^5$ is benzyl; provided that at least one of the groups $R^1$, $R^2$, and $R^3$ are hydroxy or amino.

Preferably, $R^1$ is hydroxy or amino.

When $R^2$ forms a 5 or 6 membered ring with $R^1$ preferred rings include heterocyclic rings wherein the ring contain one nitrogen atom and 4 or 5 carbon atoms. The total number of atoms includes the 2 carbon atoms of the ring to which the group (s) $R^1$ is (are) attached.

Suitable tyrphostins such as the above may be obtained by the methods disclosed in, or analogous to those of, Gazit et al 1989 and 1991, ibid, which are incorporated herein by reference.

Other PTK inhibitors include flavonoids, erbstatin, benzoquinoid ansamycin antibiotics and various peptide and nucleotide analogues. The exact nature of the PTKi will depend upon the particular target tumour for which the PTKi is to be used, taking into acount the nature of the particular PTK involved. This can be determined by those of skill in the art, for example by culture of a biopsy sample of the tumour in the presence of a range of candidate PTKs. Suitable PTKs may be found in Workman et al, Seminars in Cancer Biology, Vol 3 (1992), 369–381.

PTK inhibitors may be linked to any suitable protecting group which is removable by an enzyme. Examples of such groups include those found in WO88/07378 or in WO93/08288. For example, WO93/08288 describes "self immolative" prodrugs which can be activated by the action of a nitroreductase enzyme. These prodrugs are derivatives of p-nitrobenzyloxycarbonyl compounds.

The exact structure of the protecting group will depend upon the nature of the ADEPT or GDEPT system with which a tyrphostin prodrug is to be used. It may be any suitable group which can be removed by an enzyme or modified by the enzyme in such a manner that the group is unstable and undergoes "self immolation" to provide the active PTK.

The number of protecting groups attached to each PTKi will depend in part upon the exact structure of the inhibitor compound. It will also depend upon the relative activity of the unprotected PTKi to the PTKi when different numbers of protecting groups are added, since if additional protecting groups will achieve a reduction in potency of the prodrug this will increase the ratio of activity of PTKi to PTKi-PRT.

Desirably, one or two protecting groups will be attached to each PTKi molecule to provide a compound of the invention, although more, e.g. 3, 4 or 5 groups may be added where the PTKi is of a structure which will allow this number to be linked.

Accordingly, prodrugs according to the invention include compounds with a protecting group of the formula (II):

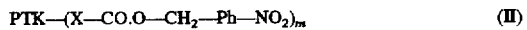

PTK—(X—CO.O—CH$_2$—Ph—NO$_2$)$_m$     (II)

where X is NH, O or S, m is an integer from 1 to 5 (e.g. 1, 2 or 3), Ph is an optionally substituted phenylene ring and PTK is a group such that PTK—(XH)$_m$ is a PTKi containing m —XH groups. The nitro group may be in the 2-position although is desirably in the 4-position of the ring relative to the Ph ring.

Within each compound of formula (II) where m from 2 to 5, each group X and Ph may be the same or different. Preferably, they are the same.

PTK inhibitors of formula (II) include tyrphostins including those of formula (I) above in which at least one of the groups $R^1$ and $R^2$ is an hydroxy, mercapto or amino group.

Suitable substituents of the phenylene ring include 1 to 4 groups which may be the same or different which are selected from fluorine, chlorine, bromine, iodine, hydroxy, mercapto, amino, nitro, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, and $C_{2-4}$ haloalkenyl. Prefeably, the substituents are from 1 to 4 fluorines in the 2, 3, 5 and 6 positions of the ring.

Preferred prodrugs according to the invention are those of formula (III):

PTK—(O—CO.O—CH$_2$—Ph—NO$_2$)$_m$     (III)

where m and Ph is as defined above and PTK is a group such that PTK—(OH)$_m$ is a PTKi compound containing m hydroxyl groups. Such prodrugs include those tyrphostins of formula (I) above in which at least one of the groups $R^1$, $R^2$ or $R^3$ is a hydroxyl group. The nitro group may be in the 2-postition although is desirably in the 4-position of the ring relative to the Ph ring.

Compounds of formulae (II) and (III) may be used as prodrugs in an ADEPT or GDEPT system in conjunction with a nitroreductase enzyme, including the E.coli nitroreductase described in WO93/08288. While the present invention is not dependent, for its definition, upon the exact mode of action of the nitroreductase on the compound of formula II or III, it is believed that the nitro group of the optionally substituted p-nitrophenyl-benzyloxy-carbonyl residue is converted to the corresponding amino or hydroxylamino group and that the resulting optionally substituted p-aminobenzyloxy-carbonyl or optionally substituted p-hydroxyl-aminobenzyloxycarbonyl compound automatically degrades under the reaction conditions used for the enzymatic reduction to release the cytotoxic compound and form optionally substituted p-aminobenzyl alcohol or optionally substituted p-hydroxylaminobenzyl alcohol and carbon dioxide as by products in accordance with the following reaction scheme:

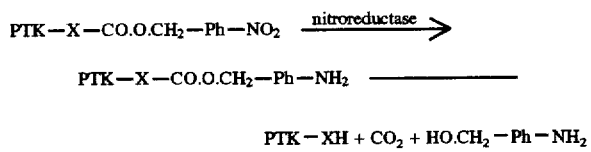

PTK—X—CO.O.CH$_2$—Ph—NO$_2$ $\xrightarrow{\text{nitroreductase}}$

PTK—X—CO.O.CH$_2$—Ph—NH$_2$

PTK—XH + CO$_2$ + HO.CH$_2$—Ph—NH$_2$

The optionally substituted p-nitrobenzyloxycarbonyl compounds of the invention are conveniently prepared by methods of chemical synthesis known per se. For example, the amine or hydroxy PTKi compounds can be reacted with optionally substituted 4-nitrobenzyl chloroformate under anhydrous conditions in the presence of a hydrogen chloride acceptor, particularly an alkylamine such as triethylamine. This reaction can be carried out in a dry aprotic organic solvent such as THF or chloroform and the resulting compound of the invention of formula II or formula III purified from the organic solvent by conventional methods such as chromatography or recrystallization. For use in ADEPT the prodrug should be unable to or have limited ability to enter cells, whereas for GDEPT the prodrug should enter cells. Accordingly, modifications may be made in the prodrug, eg in the benzene ring, to make the prodrug more, or less, lipophilic.

Similar prodrugs which can be activated by a carboxypeptidase enzyme such as carboxypeptidase G2 (CPG2) can be made using benzyl haloformate (where halo is fluoro, chloro or bromo, preferably chloro) derivatives of the formula (IV):

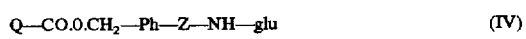

Q—CO.O.CH$_2$—Ph—Z—NH—glu     (IV)

where Q is hydrogen or fluoro, chloro or bromo, Ph is as defined above, Z is —O.CO— or —NH.CO— and glu is the residue of glutamic acid, ie a group:

—CH(CO₂H)(CH₂CH₂CO₂H)

or a di—$C_{1-6}$ alkyl ester (e.g. an ethyl or t-butyl ester) thereof, in order to provide prodrugs of the formula (V):

PTK—(X—CO.O.CH₂—Ph—Z—NH—glu)ₘ   (V)

and of the formula (VI)

PTK—(O—CO.O.CH₂—Ph—Z—NH—glu)ₘ   (VI)

where PTK is the residue of a PTKi compound such that PTK—(XH)ₘ and PTK—(OH)ₘ are as defined above, and where m, Ph, Z and glu are also as defined above. As mentioned above in connection with prodrugs of formula (II) and formula (III), for ADEPT the prodrug should have limited ability to enter cells whereas for GDEPT the prodrug may be modified if need be to make it more lipophilic in order that it does enter cells. The gamma carboxylic group of the glutamic acid may be altered to make compounds that are more lipophilic, e.g. with an aromatic or heterocyclic amide.

Within each compound of formula (V) where m from 2 to 5, each group X and Ph may be the same or different. Preferably, they are the same.

In compounds of formulae (IV), (V) and (VI), the group —Z— is in the 4-position of the ring relative to the PTK containing substituent.

Compounds of the formula (V) and (VI) in which the PTK is a tyrphostin, especially a tyrphostin of formula (I) are preferred.

The benzyl chloroformate derivatives of the formula (IV) in which Z is —NH.CO— may be made from 4-(chloromethyl)phenyl isocyanate by reaction of glutamic acid or a protected derivative thereof, eg in which both carboxy groups of the glutamic acid residue are protected with $C_{1-6}$ alkyl such as ethyl or t-butyl groups. Suitably, the reaction is carried out in a solvent such as CH₂Cl₂ at about room temperature. The resulting intermediate, [4-chloromethyl]phenyl-ureidoglutamate-di-tert-butylester, is treated in aqueous ethanol under reflux to provide the corresponding 4-hydroxymethyl compound and this is reacted with triphosgene ((CCl₃O)₂CO) in an inert solvent, eg. THF, at room temperature to provide an optionally protected compound of formula (IV). The compound when protected may be deprotected by treatment with trifluoroacetic acid or formic acid.

The benzyl chloroformate derivatives of the formula (IV) in which Z is —O.CO— may be made starting from 4-hydroxybenzaldehyde. Briefly, the aldehyde is treated with 1,2-ethane dithiol in borane trifluoroetherate plus CH₂Cl₂ at 25° C. for about 12 hours to form the 1,3 dithiolane intermediate which is treated with triphosgene as above to form the 4[1,3 dithiolane] phenylchloroformate. This is coupled with ditertbutyl-glutamate hydrochloride in dry THF in the presence of triethylamine at room temperature for about 5 hours, to provide 4[1,3 dithiolane] phenylcarbamate-glutamate-di-tbutyl. The dithiolane is deprotected with mercuric perchloroate in methanol or THF and choloroform at about 25° C. for about 5 minutes. The aldehyde is converted to the corresponding benzylic alcohol by mild reduction with sodium borohydride or other mild reducing agents at room temperature in ether and then converted to the corresponding chloroformate with triphosgene as described above.

Compounds of the formula (V) and (VI) may be made from PTK inhibitors which contain an amino or hydroxy group by analogous procedures to the methods described above for the production of compounds of formulae (II) and (III).

PTK prodrugs of the formulae (V) or (VI) will be activated by carboxypeptidases such as CPG2 by the action of the enzyme to remove the glutamic acid residue followed by "self immolation" of the remaining prodrug in a manner analogous to that described above in relation to the nitroreductases.

Prodrugs of the formula (V) where Z is —NH.CO— may also be made using novel linkers of the formula (VII):

HOH₂C—Ph—NH—CO—NH—glu   (VII)

where Ph and glu are as defined above. The optionally substituted phenylene group is substituted at the 4-position by the glu-containing moiety relative to the hydroxymethyl group.

Thus in a further aspect, the invention provides novel linkers of the formula (VII). The linkers may also be linked to other pharmaceutical compounds containing a free hydroxy, amino or mercapto group to provide novel prodrugs and such prodrugs form an additional aspect of the invention. The novel prodrugs may be prepared as pharmaceutical compositions and may be used in the treatment of patients using ADEPT or GDEPT as described herein.

The novel linkers of formula (VII) may be made from optionally substituted 4-nitrobenzyl alcohol, where the optional substituents are as defined for the group —Ph— above. The hydroxyl group of the 4-nitrobenzyl alcohol is protected, for example by reaction with tert-butyl-diphenyl-chloro-silane at room temperature in an organic solvent, to provide an optionally substituted (4-nitro-benzyl) tert-butyl-di-phenyl-silyl ether. The 4-nitro group is then reduced to an amine group by catalytic hydrogenation or catalytic hydrogen transfer, for example with ammonium formate in the presence of a catalyst such as Pd/C in a protic solvent such as an alcohol, e.g. methanol or ethanol.

The amine group may then converted into an isocyanate group for example by reaction with phosgene, diphosgene or triphosgene in the presence of a tertiary organic amine such as triethylamine and an aprotic organic solvent with a boiling point higher than 50° C. such as toluene. The isocyanate compound is then reacted with di-$C_{1-6}$alkyl-glutamic acid or derivative thereof, eg di-$C_{1-6}$alkyl-glutamate hydrochloride. This may be done at room temperature in the presence of triethylamine in an aprotic organic solvent such as toluene, THF or dichloromethane.

Alternatively, the amine compound may be reacted directly in a one-pot synthesis with the di-$C_{1-6}$alkyl-glutamic acid or derivative thereof in the presence of triphosgene and triethylamine in an aprotic solvent such as THF or dichloromethane.

In either case, the resulting compound is treated to remove the hydroxy-protecting group, for example by the use of tetra-butylammonium fluoride in THF at room temperature.

The resulting compound of formula (VII) where glu is in the form of a di-$C_{1-6}$alkyl ester may be deprotected to remove the ester groups for example by the use of an acid such as formic or trifluoro acetic acid. Alternatively, it may be linked to a PTKi containing a group —OH, —NH₂ or —SH by reaction with the PTKi or activated derivative thereof in aprotic solvents such as dichloromethane and/or THF in the presence of a tertiary organic base such as triethylamine at room temperature, to provide a compound of the formula (V). The di-$C_{1-6}$alkyl ester groups of the compound, if present, may be removed as described above.

In order to link a PTKi with a group —XH to the novel linker of formula (VII) the group —XH may be converted to a reactive chloroformyl, chlorothioformyl or isocyanate derivative by the use of phosgene, diphosgene or triphosgene in the presence of a phase transfer catalyst such as tetra-butyl ammonium hydrogen sulphate. The reaction may be carried out in the presence of a base such as NaOH in an organic solvent such as toluene, THF or dichloromethane.

In a further aspect of the invention, prodrugs of the formula (V) in which Z is —O.CO— may be made using novel linkers of the formula (VIII):

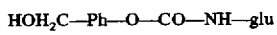   (VIII)

where Ph and glu are as defined above. The optionally substituted phenylene group is substituted at the 4-position by the glu-containing moiety relative to the hydroxymethyl group.

Thus in a further aspect, the invention provides novel linkers of the formula (VIII). The linkers may also be linked to other pharmaceutical compounds containing a free hydroxy, amino or mercapto group to provide novel prodrugs and such prodrugs form an additional aspect of the invention. The novel prodrugs may be prepared as pharmaceutical compositions and may be used in the treatment of patients using ADEPT or GDEPT as described herein.

To produce a compound of formula (VIII), optionally substituted 4-hydroxybenzaldehyde is protected as a 1,3-dithiane or dithiolanein in an aprotic solvent such as $CH_2Cl_2$ in the presence of $BF_3.Et_2O$, at room temperature by reaction with 1,3-propanedithiol or 1,2-ethanedithiol, to give the corresponding 4(1',3'-dithianyl) phenol or 4(1',3'-dithidanyl) phenol. This compound is coupled with di—$C_{1-6}$alkyl-glutamyl isocyanate, in an aprotic solvent such as toluene in the presence of a tertiary organic amine such as triethylamine, to the corresponding O[4(1',3'-dithianyl)-phenyl]N(di—$C_{1-6}$alkyl-glutamyl)carbamate. The deprotection of the carbamate to the corresponding aldehyde, may be carried out with $Hg(ClO_4)_2$ or $Tl(NO_3)_3$ in THF or dichloromethane at room temperature. The reduction of the aldehyde yields the desired O(4-benzyl-oxy)N(di—$C_{1-6}$alkyl-glutamyl) carbamate. This may be deprotected by treatment with an acid such as trifluoroacetic or formic acid to remove the alkyl ester protecting groups to provide a prodrug of formula (V).

The novel linkers of formula (VIII) may be attached to PTKi compounds or other pharmaceutical compounds containing a free hydroxy, amino or mercapto group in the same way as described above for the linkers of formula (VII). Thus the invention further provides a compound which is a prodrug of an active drug wherein the active drug has at least one free amino, hydroxyl or mercapto group which is/are linked to one or more (e.g. from 1 to 5, e.g. 1, 2 or 3) linkers of the formulae (VII) or (VIII), each of which may be the same or different.

Other suitable PTKi prodrugs (including tyrphostins such as those of formula (I)) include those which are derivatized with a sugar or a β-lactam derivative. For example, suitable linkers which may be attached to PTK inhibitors of the type PTK—$NH_2$ or PTK—OH or PTK—SH described above are:

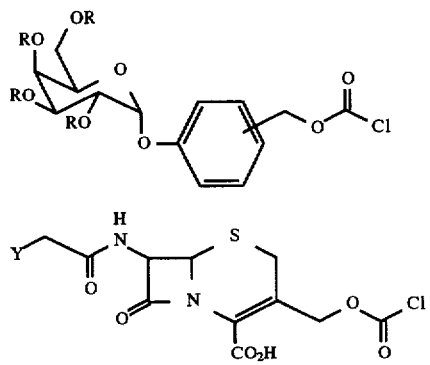

where R is hydrogen or acetyl and Y is aryl such as phenyl, benzyl or tolulyl, and these may be made in an analogous manner to the other prodrugs described above.

Any hydroxy, amino or mercapto group of a PTKi may be linked in the manner described above to provide a prodrug of the present invention. If desired, more than one such group may be derivatized to make a prodrug. If however only a single hydroxy, mercapto or amino group is to be reacted to form a prodrug, any remaining groups of the PTK may be protected with for example tbutyl or adamantyl groups (in the case of hydroxyl) or butyloxycarbonyl groups in the case of amino. Such protecting groups may be attached using chemical processes known in the art. The groups of the PTKi to be reacted with the linker may be derivatized to the corresponding haloformate or isocyanate and then coupled with the linkers such as those of formulae (VII) or (VIII). After the PTKi prodrug has been made, the protecting groups may be removed by conventional means, eg by treatment with trifluoroacetic acid.

Physiologically acceptable derivatives of said prodrug include salts, amides, esters and salts of esters. Esters include carboxylic acid esters in which the non-carbonyl moiety of the ester grouping is selected from straight or branched chain $C_{1-6}$alkyl, (methyl, n-propyl, n-butyl or t-butyl); or $C_{3-6}$cyclic alkyl (e.g. cyclohexyl). Salts include physiologically acceptable base salts, eg derived from an appropriate base, such as alkali metal (e.g. sodium), alkaline earth metal (e.g. magnesium) salts, ammonium and $NR_4$ (wherein R is $C_{1-4}$ alkyl) salts. Other salts include acid addition salts, including the hydrochloride and acetate salts. Amides include non-substituted and mono- and di-substituted derivatives.

The invention further provides pharmaceutical formulations. Such formulations comprise a compound of the invention together with one or more pharmaceutically acceptable carriers or diluents.

Pharmaceutically acceptable carriers or diluents include those used in formulations suitable for oral or parenteral (e.g. intramuscular or intravenous) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

Suitable liposomes include, for example, those comprising the positively charged lipid (N[1-(2,3-dioleyloxy)propyl]-N,N,N-triethylammonium (DOTMA), those comprising dioleoyl-phosphatidylethanolamine (DOPE), and those comprising 3β[N-(n',N'-dimethylaminoethane)-carbamoyl] cholesterol(DC-Chol).

The PTKi prodrugs of the present invention and the antibody/enzyme conjugate for ADEPT can be administered simultaneously but it is often found preferable, in clinical practice, to administer the enzyme/agent conjugate before the prodrug, e.g. up to 72 hours or even 1 week before, in order to give the enzyme/agent conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour the premature release of the PTKi agent is minimised.

In VDEPT the prodrug will usually be administered following administration of the modified virus encoding an enzyme. Typically, the virus will be administered to the patient and then the uptake of the virus by infected cells monitored, for example by recovery and analysis of a biopsy sample of targeted tissue. Similarly in GDEPT the prodrug will usually be administered following the administration of a delivery system containing the gene encoding the enzyme.

In ADEPT the degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to the such part of the conjugate so as to inactivate the enzyme and/or accelerate the clearance of the conjugate from the blood. Such a component may include an antibody to the enzyme component of the system which is capable of inactivating the enzyme.

The second component may be linked to a macromolecule such as dextran, a liposome, albumin, macroglobulin or a blood group O erythrocyte so that the second component is restrained from leaving the vascular compartment. In addition or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be administered and designed for use such that it will not, to any appreciable extent, enter the extravascular space of the tumour where it could inactivate localised conjugate prior to and during administration of the prodrug.

The exact dosage regime for both GDEPT and ADEPT will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of both the prodrug and either the enzyme/agent conjugate or modified virus and administration by the intravenous route is frequently found to be the most practical. In ADEPT systems, the dose of the prodrug and conjugate will ultimately be at the discretion of the physician, who will take into account such factors as the age, weight and condition of the patient. Suitable doses of prodrug and conjugate are given in Bagshawe et al. Antibody, Immunoconjugates, and Radiopharmaceuticals (1991), 4, 915–922. A suitable dose of conjugate may be from 500 to 200,000 enzyme units/m$^2$ (e.g. 20,000 enzyme units/m$^2$) and a suitable dose of prodrug may be from 5 to 2000 mg/m$^2$ (e.g. 200 mg/m$^2$).

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug, but usually there will be an adequate concentration of the conjugate at the site of desired treatment within 48 hours.

In GDEPT systems, the amount of virus or other vector delivered will be such as to provide a similar cellular concentration of enzyme as in the ADEPT system mentioned above. This may be determined by clinical trials which involve administering a range of trial doses to a patient and measuring the degree of infection or transfection of a target cell or tumour. The amount of prodrug required will be similar to or greater than that for ADEPT systems.

The present invention also provides a system for use in the control of neoplasia in a human or animal subject comprising an enzyme capable of converting a PTKi prodrug to an active PTKi, preferably conjugated with a targeting agent such as monoclonal antibody that will bind to a tumour-associated antigen, in association with a prodrug as defined above. When the enzyme is a nitroreductase, the system also preferably comprises a suitable cofactor for the enzyme. Suitable cofactors include a riboside or ribotide of nicotinic acid or nicotinamide.

The present invention extends to a method of treating neoplasia in a human or animal subject requiring such treatment which comprises administering to the host an effective amount of a PTKi prodrug of the invention and an enzyme, preferably conjugated with a targeting agent such as a monoclonal antibody that will bind to a tumour-associated antigen.

The present invention also provides a system for use in the control of neoplasia in a human or animal subject comprising a modified virus or other delivery system capable of selectively infecting tumour cells in said subject, said virus carrying a DNA or RNA sequence encoding an enzyme, in association with a PTKi prodrug capable of being converted to a PTKi by the action of said enzyme.

The present invention extends to a method of treating neoplasia in a human or animal subject requiring such treatment which comprises administering to the host an effective amount of a PTKi prodrug of the invention and a modified virus, said modified virus capable of selectively infecting tumour cells in said subject, said virus carrying a DNA or RNA sequence encoding an enzyme capable of converting said PTKi prodrug to an active PTKi.

The present invention also extends to a method of treating neoplasia in a human or animal subject requiring such treatment which comprises administering to the host an effective amount of a PTKi prodrug of the invention and a non viral vector system, said non-viral vector system capable of being selectively introduced into tumour cells in said subject, said vector system carrying a DNA or RNA sequence encoding an enzyme capable of converting said PTKi prodrug to an active PTKi operably linked to a promoter effective in expressing said enzyme in said cells.

11

The various systems for use in the treatment of neoplasia by ADEPT described above optionally include the "second component" for accelerated clearance described above. Likewise, the methods of treatment of neoplasia described above optionally include as part of that method the use of the second component, an effective amount of which is administered after administration of the enzyme, in order to increase the ratio of localised to freely circulating enzyme. Reference may be made to WO89/10140 for further particular details of the second component, and such details can be incorporated for use in the present invention.

Modified viruses capable of selectively infecting tumour cells are known in the art. By "selectively infecting" it is meant that the virus will primarily infect tumour cells and that the proportion of non-tumour cells infected is such that the damage to non-tumour cells by administration of the PTKi prodrug will be acceptably low, given the nature of the disease being treated. Ultimately, this will be determined by the physician.

It will also be understood that the DNA or RNA sequence encoding an enzyme carried by the virus will be linked to suitable expression control signals such that expression of the enzyme will occur in the targeted tumour cells.

The non-viral vector system will be capable of being selectively introduced into tumour cells utilizing methods such as those mentioned above, e.g. calcium phosphate co-precipitation, microinjection, liposomes, direct DNA uptake, and receptor-mediated DNA transfer (Morgan & French Anderson, Annu. Rev. Biochem., 1993,62;191).

Suitable monoclonal antibodies for use in the present invention include antibodies to cerbB2, such as ICR12 (Bakir, M A et al, J. Nucl. Med (1992) 33;2154–2160), and antibodies to epidermal growth factor receptor, such as ICR16 (Dean, C J et al, Int. J. Cancer Suppl. 8,(1994), 103).

As used herein, the term "monoclonal antibody" will be understood by those of skill in the art not simply to refer to antibodies produced by traditional hybridoma techniques, but also to cover antibodies and variants thereof produced by recombinant means. These include, for example, humanised antibodies such as those with a constant region from a human antibody grafted onto a non-human antibody variable region (see for example EP-A-O 120 694), chimeric antibodies such as those with non-human complementarity determining regions (CDRs) grafted into a human variable region framework (see for example EP-A-O 239 400) and single chain antibodies. Fragments of such monoclonal antibodies which retain their target binding activity are also included by the general term "monoclonal antibody". This includes Fv, Fab' and F(ab')$_2$ fragments. It also includes recombinant or synthetic proteins based upon the CDRs of such antibodies, e.g. abzymes (a polypeptide with both antibody-like binding acitivity and enzyme activity) and diabodies.

Prodrugs of the present invention may also be used as reagents in in vitro systems to test the activity of candidate enzymes or antibodies which may be incorporated into ADEPT or GDEPT systems.

For example, a tumour cell line carrying a marker to which an antibody is directed may be grown in vitro, and then an antibody-enzyme conjugate added to the culture. The enzyme will be one which is, or suspected to be, capable of converting a prodrug of the invention into an active drug. The prodrug is then added to the culture and the amount of cell killing or inhibition of cell growth is measured (for example by using a vital stain to record the number of viable cells or by replating a sample of the culture to count the number of viable cells).

12

EXAMPLES

The following examples illustrate the invention. The reaction schemes which follow further illustrate these examples.

All starting materials, reagents and anhydrous solvents (THF under N$_2$) were purchased from Aldrich, unless otherwise stated. The di-tert-butyl glutamate is commercially available from Sigma. Kiselgel 60 (0.043–0.060) was used in gravity columns (Art 9385 and 15111, Merck). TLC was performed on precoated sheets of Kiselgel 60 F$_{254}$ (Art 5735, Merck). Electron Impact spectra were determined with a VG 7070H mass spectrometer and a VG 2235 data system using the direct-insertion method, an ionizing energy of 70 eV, trap current of 100 mA and an ion-source temperature at 180°–200° C. FAB mass spectra were determined using xenon gas. High resolution accurate mass spectra were determined on the same systems. Reported spectra are by FAB unless otherwise stated. NMR spectra were determined in Me$_2$SO—d$_6$ on a Brucker AC250 spectrometer (250 MHz) at 30° C. (303 K) unless otherwise stated. I.R. spectra (film) were recorded on a Perkin Elmer 1720X FT-I.R. spectrometer.

EXAMPLE 1

Summary

A tyrphostin prodrug, N$^1$(4-hydroxybenzyl)N$^3$(di-tert-butyl-glutamyl) urea, 8 (See Scheme 1) clearable by the enzyme CPG2 was made. This compound is designed to be coupled to the hydroxy, mercapto or amino functional groups of tyrphostin compounds. The intermediate N$^1$(4-hydroxybenzyl)N$^3$(di-tert-butyl-glutamyl) urea 8, was synthesised for coupling to tyrphostin drugs according to the Scheme 1. The starting material, 4-nitrobenzylic alcohol, 1, was protected as tert-butyl-di-phenyl-silyl ether, 2, by reacting with tert-butyl-diphenyl-chlorosilane and imidazole in DMF (or THF) at room temperature. The protected nitro derivative, 2, was reduced by hydrogen transfer with ammonium formate (Pd/C 10% in EtOH). The amine, 3, thus formed was reacted with triphosgene in toluene at 70° C., to form the corresponding isocyanate 4. The protected linker, 7, was obtained by coupling the isocyanate 4 with di-tert-butyl-glutamate in THF in the presence of NEt$_3$ at room temperature. An alternative route to 7 was by the direct coupling of amine 3 with the di-tert-butyl-glutamyl isocyanate 6, under the same conditions as described above, where the di-tert-butyl-glutamyl isocyanate 6 was obtained from the di-tert-butyl-glutamate by treatment with triphosgene and NEt$_3$ in toluene at −78° C. Using this route, the compound 7 was obtained in good yield from the amine 3 and di-tert-butyl-glutamate in a one-pot synthesis.

The compound 7 was deprotected by Bu$_4$NF in THF at room temperature and the di-tert-butyl ester of the linker, 8, purified by column chromatography. The ester 8 was reacted with 4-chloroformyl-benzilydene-malononitrile, 10, resulting in the di-tert-butyl ester linker of the tyrphostin 11. A phase transfer catalysis system was utilised since the phosgenation of the 4-hydroxy-benzilydene-malononitrile 9, which would be the usual procedure of choice, resulted only in the corresponding carbonate. The phase transfer method used tetra-butylammonium hydrogen sulphate as catalyst and led to a high yield of the desired compound. The final deprotection to compound 12 was carried out using formic acid at 4° C.

Experimental (4-nitro-benzyl) tert-butyl-di-phenl-silyl ether (2)

To a stirred solution of 4-nitrobenzyl alcohol, 1, (1.00 g, 6.50 mmol), and imidazole (0.97 g, 14.1 mmol) in DMF (10.0 mL), was added tert-butyl-diphenyl-chlorosilane (1.98 g, 7.20 mmol) over 10 min under $N_2$ at room temperature. The reaction mixture was stirred for an additional 5 h, diluted with $Et_2O$ (75 mL), washed with $H_2O$ (5×15 mL), dried ($MgSO_4$) and evaporated to dryness under vacuum. An oil was obtained which crystallised on standing and was recrystallised to a solid from EtOH (70%); yield: 2.36 g (93.%). $v_{max}/cm^{-1}$ (film): 2931, 2857 ($CH_2$, asym., sym. ), 1521, 1345 ($NO_2$); $^1H$—NMR, $d_H$: 1.06(9H, s, t-Bu.), 4.92 (2H, s, $CH_2$), 7.42–7.46 (5H, m, Ph), 7.63–7.65 (7H, m, Ph+$H_{arom2+6}$), 8.23 (2H, d, J=8.23, $H_{arom3+5}$); MS, (EI), (391.54); m/z: 334 (M—t-Bu, 100), 288 (M—t-Bu—$NO_2$, 10), 256 (M—t-Bu—Ph, 20), 199 ($Ph_2SiOH^+$, 100); $C_{23}H_{25}NO_3Si$.

(4-amino-benzyl) tert-butyl-di-phenyl-silyl ether (3)

To a stirred solution of 2 (5.00 g, 12.77 mmol) in ethanol (100 mL) was added Pd/C (10%, 1.50 g) and ammonium formate (4.60 g) at room temperature. After 1.5 h the catalyst was removed by filtration, the filtrate concentrated to dryness under vacuum and the residue partitioned between EtOAc:$H_2O$. The organic layer was dried ($MgSO_4$) and concentrated under vacuum to give 3 as an oil; yield: 4.24 g (92%); $v_{max}/cm^{-1}$ (film): 3433, 3378 ($NH_2$), 2931, 2857 ($CH_2$, asym., sym.); $^1H$—NMR, $d_H$: 1.00 (9H, s, t-Bu), 4.57 (2H, s, $CH_2$), 4.98 (2H, s broad, $NH_2$), 6.52 (2H, d, J=8.25, $H_{arom3+5}$), 6.96 (2H, d, $H_{arom2+6}$), 7.42–7.46 (5H, m, Ph), 7.62–7.65 (5H, m, Ph); MS, (EI), (361.56); m/z: 361 ($M^+$, 8), 304 (M—t-Bu, 100), 199 ($Ph_2SiOH^+$, 100); $C_{23}H_{27}NOSi$.

(4-isocyanato-benzyl)tert-butyl-di-phenyl-silyl ether (4)

To a stirred solution of 3 (0.63 g, 1.70 mmol) and triethylamine (0.16 g, 0.60 mmol) in toluene (10 mL) at 70° C., was added triphosgene (0.18 g, 1.7 mmol). After 5 h the reaction mixture was filtered and the filtrate evaporated to an oil under vacuum; yield: 0.65 g (99%) which was used without further purification; $v_{max}/cm^{-1}$ (film): 2931, 2857 ($CH_2$, asym., sym.), 2275 (NCO); $^1H$—NMR, $d_H$: 1.03 (9H, s, t-Bu), 4.76 (2H, s, $CH_2$), 7.23 (2H, d, J=8.38, $H_{arom3+5}$), 7.35 (2H, d, $H_{arom2+6}$), 7.37–7.48 (5H, m, Ph), 7.62–7.71 (5H, m, Ph); MS, (EI), (387.55); m/z: 330 (M—t-Bu, 52), 286 (M—t-Bu, M—t-Bu—NCO, 48), 199 ($Ph_2SiOH^+$, 100); $C_{24}H_{25}NO_2Si$.

$N^1$(4 -tert-butyl-di-phenyl-silyl-O-benzyl) $N^3$ (di-t-butyl-glutamyl) urea (7)

Method A: To a solution of di-tert-butyl-glutamate hydrochloride (0.46 g, 1.55 mmol) in THF (7 mL) was added triethylamine (0.31 g 3.10 mmol). The isocyanate, 4, (0.60 g, 1.55 mmol) in dry THF (3 mL) was added to the glutamate ester at room temperature. After 2 h the reaction mixture was filtered and evaporated to dryness under vacuum. The product was purified by column chromatography (EtOAc : cyclohexane 2:1) resulting in the oil, 7; yield 0.53 g (53%). $v_{max}/cm^{-1}$ (film): 3359 (NH), 2932, 2857 ($CH_2$, asym., sym.), 1729 (C=O, ester), 1670 (C=O, urea), 1154 (C—O, str.); $^1H$—NMR, $d_H$: 1.03 (9H, s, t-Bu) , 1.40 (9H, s, t-Bu-glu) , 1.43 (9H, s, t-Bu-glu), 1.68–2.00 (2H, 2 m, CH(NH)$CH_2$) , 2.18–2.32 (2H, 2 m, $CH_2CO_2$—t-Bu), 4.08–4.12 (1H, m, CH(NH)$CH_2$), 4.68 (2H, s, $CH_2$), 6.38 (1H, d, J=8.12, NH—glu) , 7.19 (2H, d, J=8.41, $H_{arom3+5}$), 7.32–7.47 (7H, m, Ph+$H_{arom2+6}$), 7.62–7.70 (5H, m, Ph), 8.54 (1H, s, NH—Ph); MS, (EI), (646.90); m/z: 540 (M—t-Bu+1, 2), 534 (M—2t-Bu+2, 5), 478 (M—3t-Bu+3, 100), 199 ($Ph_2SiOH^+$, 100); $C_{37}H_{50}N_2O_6Si$.

Method B: (one pot synthesis of compound 7) To a solution of di-tert-butyl-glutamate hydrochloride (4.14 g, 14.0 mmol) and triphosgene (1.39 g, 4.67 mmol) in toluene at −78° C., triethylamine (2.83 g, 28.0 mmol) in toluene (10 mL) was added dropwise over 30 min. The reaction was allowed to warm to room temperature. After 50 min, a solution containing (4-aminobenzyl)tert-butyl-diphenyl-silyl ether, 3 (5.00 g, 13.8 mmol) and triethylamine (1.95 mL, 14.0 mmol) was added over 5–10 min. After 20 h, the reaction mixture was filtered, washed sequentially with: $H_2O$ (200 mL), aq HCl (1%, 200 mL), aq $Na_2CO_3$ (1%, 200 mL), $H_2O$ (2×200 mL) dried ($Mg_2SO_4$) and evaporated to an oil under vacuum; yield: 9.90 g. This product was deprotected without further purification.

$N^1$(4-hydroxyhenzyl)$N^3$(di-tert-butyl-glutamyl) urea (8)

From Method A- To a solution of 7, (0.53 g, 0.80 mmol) in THF (10 mL) was added tetra-butylammonium fluoride (2.5 mL, 2.5 mmol of 1M solution) in THF at room temperature. After 3 h, the reaction mixture was evaporated to dryness under vacuum. The product was dissolved in EtOAc (20 mL) , washed with $H_2O$ (2×10 mL), dried ($MgSO_4$) and evaporated to an oil; yield: 0.40 g.

The deprotected compound, 8 (0.38 g), was purified by column chromatography (EtOAc: cyclohexane 3:1) resulting in an oil which crystallised on standing; yield 0.093 g (29.%). $v_{max}/cm^{-1}$ (film): 3370 (broad, NH+OH), 2967 ($CH_3$), 2930, 2857 ($CH_2$, asym., sym.), 1716 (C=O, ester), 1678 (C=O, urea), 1153 (C—O, str.); $^1H$—NMR, $d_H$: 1.40 (9H, s, t-Bu) , 1.42 (9H, s, t-Bu), 1.72–2.00 (2H, 2 m, CH(NH)$CH_2$) , 2.20–2.31 (2H, 2 m, $CH_2CO_2$—t-Bu), 4.10–4.18 (1H, m, CH(NH)$CH_2$), 4.39 (2H, d, J=5.36, $CH_2$), 4.99 (1H, t, $CH_2OH$), 6.38 (1H, d, J=8.11, NH—glu), 7.16 (2H, d, J=8.35, $H_{arom3+5}$), 7.31 (2H, d, $H_{arom2+6}$), 8.50 (1H, S, NH—Ph); MS, (EI), (408.94); m/z: 408 ($M^+$, 10), 352 (M—t-Bu+1, 4), 296 (M—2t-Bu+2, 14); $C_{21}H_{32}N_2O_6$.

From Method B- The one pot procedure yielded 8, which was purified by column chromatography; yield 2.57 g (46% over three steps) which was recrystallised from aq MeOH (60%).

(4-chloroformyl-benzylidene) malononitrile (10)

The Na salt of 4-chloroformyl-benzylidene malononitrile, 9 (0.34 g, 2.0 mmol), was made in aq NaOH (10 mL, 0.10 g, 2.5 mmol ) To this solution was added the phase transfer catalyst, tetra-butyl ammonium hydrogen sulphate (0.070 g, 0.2 mmol) in $CH_2Cl_2$ (8 mL) with vigorous stirring. To this was added a solution of phosgene (20%, 0.40 g, 4.0 mmol) in toluene at room temperature. After 30 min the organic layer was separated, washed with $H_2O$, dried ($MgSO_4$) and evaporated to a solid under vacuum; yield: 0.39 g (84%). $v_{max}/cm^{-1}$ (film): 2230 (CN), 1784 (C=O, chloroformate), 1199, 1166 (C—O, str.); $^1H$—NMR, ($CDCl_3$), $d_H$: 7.50 (2H, d, J=8.81, $H_{arom3+5}$), 7.79 (1H, s, $H_{vinyl}$) , 8.02 (2H, d, $H_{arom2+6}$); MS, (EI) , (232.63); m/z: 232 ($M^+$, 100); $C_{11}H_5N_2O_2Cl$.

$N^1$[(4-benzylidene-malononitrile-oxy-carbonyl)-4-oxy benzyl)]$N^3$(di-tert-butyl-glutamyl) urea (11)

To a solution of 10 (1.5 mmol) in $CH_2Cl_2$ (10 mL) was added $N^1$(4-hydroxybenzyl)$N^3$(di-t-butyl-glutamyl) urea, 8 (0.41 g, 1.0 mmol) in dry TMF (12.5 mL) and triethylamine (0.25 mL, 1.65 mmol) at room temperature under $N_2$. After 22 h, the reaction mixture was evaporated to a volume of 5 mL, dissolved in EtOAc (20 mL), washed sequentially with $H_2O$ (2×20 mL), aq NaOH (1%, 20 mL), $H_2O$ (2×20 mL), dried ($MgSO_4$) and evaporated under vacuum to an oil which was purified by column chromatography (EtOAc: cyclohexane 3:1) resulting in a solid; yield 0.28 g (65%) (0.12 g of the starting material 8 was recovered). $v_{max}/cm^{-1}$ (film): 3369 (NH), 2924, 2857 ($CH_2$, asym., sym.), 1765 (C=O, carbonate), 1728 (C=O, ester), 1658 (C=O, urea), 1216, 1153 (C—O, str.); $^1$H—NMR, $d_H$: 1.40 (9H, s, t-Bu) , 1.43 (9H, s, t-Bu) , 1.80–2.00 (2H, 2 m, CH(NH) CH$_2$), 2.22–2.35 (2H, 2 m, CH$_2$CO$_2$—t-Bu), 4.10–4.20 (1H, m, CH(NH) CH$_2$), 5.21 (2H, s, CH$_2$), 6.46 (1H, d, J=8.10, NH—glu), 7.33 (2H, d, J=8.48, H$_{arom3+5}$-cmpd 8), 7.42 (2H, d, H$_{arom2+6}$-cmpd 8), 7.53 (2H, d, J=8.67, H$_{arom3+5}$-cmpd 9), 8.02 (2H, d, H$_{arom2+6}$-cmpd 9), 8.54 (1H, s, NH—Ph), 8.68 (1 h, s, H$_{vinyl}$); MS, (604.59); m/z: 391 (M—169—CO$_2$, 2), 279 (M—169—CO$_2$-2t-Bu+2, 30) (169=cmpd 9-1); C$_{32}$H$_{36}$N$_4$O$_8$.

N$^1$[(4-benzylidene-malononitrile-oxy-carbonyl)-4-oxy benzyl)]N$^3$glutamyl urea (12)

Compound, 11 (0.05 g,0.08 mmol) was dissolved in formic acid (95%, 6.0 mL), at 4° C. under N$_2$. After 22 h the solvent was evaporated under vacuum (pump) to give a solid; yield: 0.037 g (91%). $v_{max}$/cm$^{-1}$ (film): 3370 (v. broad, NH+OH), 2930, 2857 (CH$_2$, asym., sym. ) , 1719 (C=O, ester) , 1681 (C=O, urea), 1221, 1176 (C—O, str.); $^1$H—NMR, $d_H$: 1.80–2.10 (2H, 2 m, CH(NH)CH$_2$) , 2.20–2.35 (2H, 2 m, CH$_2$CO$_2$H) , 4.20–4.30 (1H, m, CH(NH)CH$_2$), 5.07 (2H, s, CH$_2$), 6.47 (1H, d, J=7.86, NH—glu), 6.80 (2H, d, J=8.76, H$_{arom3+6}$-cmpd 9), 7.25 (2H, d, J=8.39, H$_{arom3+5}$-cmpd 8) , 7.39 (2H, d, H$_{arom2+6}$-cmpd 8) , 7.89 (2H, d, H$_{arom2+6}$-cmpd 9), 8.29 (1H, s, NH—Ph), 8.69 (1 h, s, H$_{vinyl}$); MS, (492.44); m/z: 323 (M—169, 18), 277 (M—169—CO$_2$, 18) (169=cmpd 9- 1); C$_{24}$H$_{20}$N$_4$O$_8$.

EXAMPLE 2

Summary

Two tyrphostin prodrugs were designed which could be activated by the enzyme nitroreductase. These are 4(4-nitro-phenyl-oxy-carbonyl)oxy-benzylidene-malononitrile, 15a, and 3,4-di(4-nitro-phenyl-oxy-carbonyl)oxy-benzylidene-malononitrile, 15b, (See Scheme 2). For these syntheses, 4-hydroxy-benzilydene-malononitrile, 13a, and 3,4-dihydroxy-benzilydene-malononitrile, 13b were coupled with 4-nitrobenzyl-chloroformate 14, leading to the desired prodrugs, 15a and 15b respectively.

Experimental

4(4-nitro-phenyl-oxy-carbonyl)oxy-benzylidene-malononitrile (15a)

To a solution of 4-hydroxy-benzylidene-malononitrile, 13a (0.50 g, 2.93 mmol), in dry THF (10 mL), was added 4-nitro-benzyl chloroformate, 14 (0.63 g, 2.92 mmol) and triethylamine (0.30 g, 3.0 mmol) at an initial temperature of 4° C. After 2.5 h, the reaction mixture was filtered and the filtrate evaporated to dryness under vacuum. The residue thus obtained was partitioned against EtOAc: H$_2$O (1:1, 25 mL), the organic layer washed sequentially with aq NaOH (2%, 25 mL), aq HCl (2%, 25 mL) and H$_2$O (2×25 mL), dried (MgSO$_4$) and evaporated to a solid under vacuum; yield: 0.55 g (54.%), which was recrystallised from EtOH. $v_{max}$/cm$^{-1}$ (film): 2230 (CN), 1767 (C=O, carbonate), 1522, 1349 (NO$_2$), 1221 (C—O, str.); $^1$H—NMR, $d_H$: 5.46 (2H, s, CH$_2$) , 7.55 (2H, d, J=8.77, H$_{arom3+5}$) , 7.73 (2H, d, J=8.70, H$_{arom2+6}$—PhNO$_2$) , 8.03 (2H, d, H$_{arom2+6}$) , 8.27 (2H, d, H$_{arom3+5}$—PhNO$_2$), 8.55 (1H, s, H$_{vinyl}$); MS, (EI), (349.30); m/z: 349 (M$^+$, 3), 305 (M—CO$_2$, 60); C$_{18}$H$_{11}$N$_3$O$_5$.

3,4-di(4-nitro-phenyl-oxy-carbonyl)oxy-benzylidene-malono nitrile (15b)

A similar procedure was used for 3,4-di-hydroxy-benzylidene-malononitrile, 13b (0.50 g, 2.70 mmol) resulting in a solid; yield: 0.86 g, (59.%) which was recrystallised from EtOH. $v_{max}$/cm$^{-1}$ (film): 2232 (CN), 1776 (C=O, carbonate), 1523, 1350 (NO$_2$), 1247 (C—O, str.); $^1$H—NMR, $d_H$: 5.44 (4s, CH$_2$), 7.66 (4H, d, J=8.65, H$_{arom2+6}$-2PhNO$_2$), 7.79 (1H, d, J=8.40, H$_{arom5}$), 7.99 (1H, q, H$_{arom6}$), 8.01 (1H, d, H$_{arom2}$), 8.18 (2H, d, H$_{arom3+5}$-PhNO$_2$') , 8.19 (2H, d, H$_{arom3+5}$-PhNO$_2$") , 8.56 (1H, s, H$_{vinyl}$).

EXAMPLE 3

Summary and Experimental

O(4-hydroxybenzyl)N(di-tert-butyl-glutamyl) carbamate, 20 (See Scheme 3), another self-immolative linker, was prepared. Compound 16, 4-hydroxy-benzaldehyde, was protected with 1,3-propane-dithiol in CH$_2$Cl$_2$ in the presence of BF$_3$.Et$_2$O, at room temperature, to give the 4(1',3'-dithianyl) phenol, 17, in good yield. Coupling of 17 with di-tert-butyl-glutamyl isocyanate, 6, in toluene in the presence of Et$_3$N, led to the O[4(1',3'-dithianyl)-phenyl]N(di-tert-butyl-glutamyl)carbamate, 18. The deprotection of the carbamate, 18, to the corresponding aldehyde, 19, was carried out with Hg(ClO$_4$)$_2$ in THF at room temperature. The reduction of 19 yielded the desired O(4-benzyl-oxy)N(di-tert-butyl-glutamyl) carbamate, 20. This is coupled to the tyrphostin of 10 as described above in Example 1 and the ester protecting groups are removed.

SCHEME 1

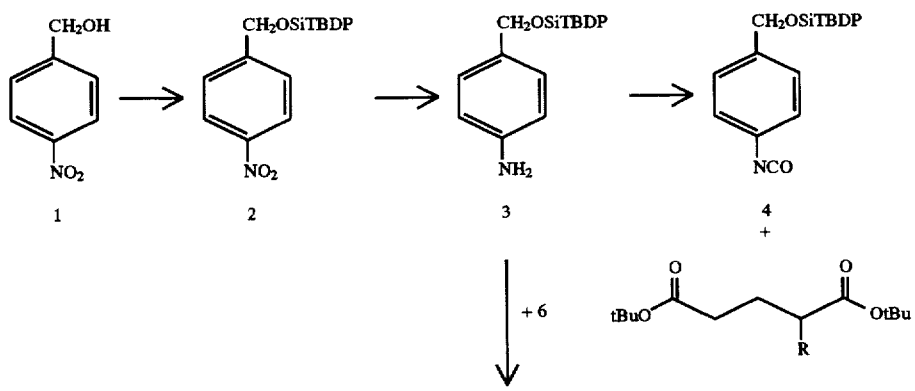

-continued
SCHEME 1
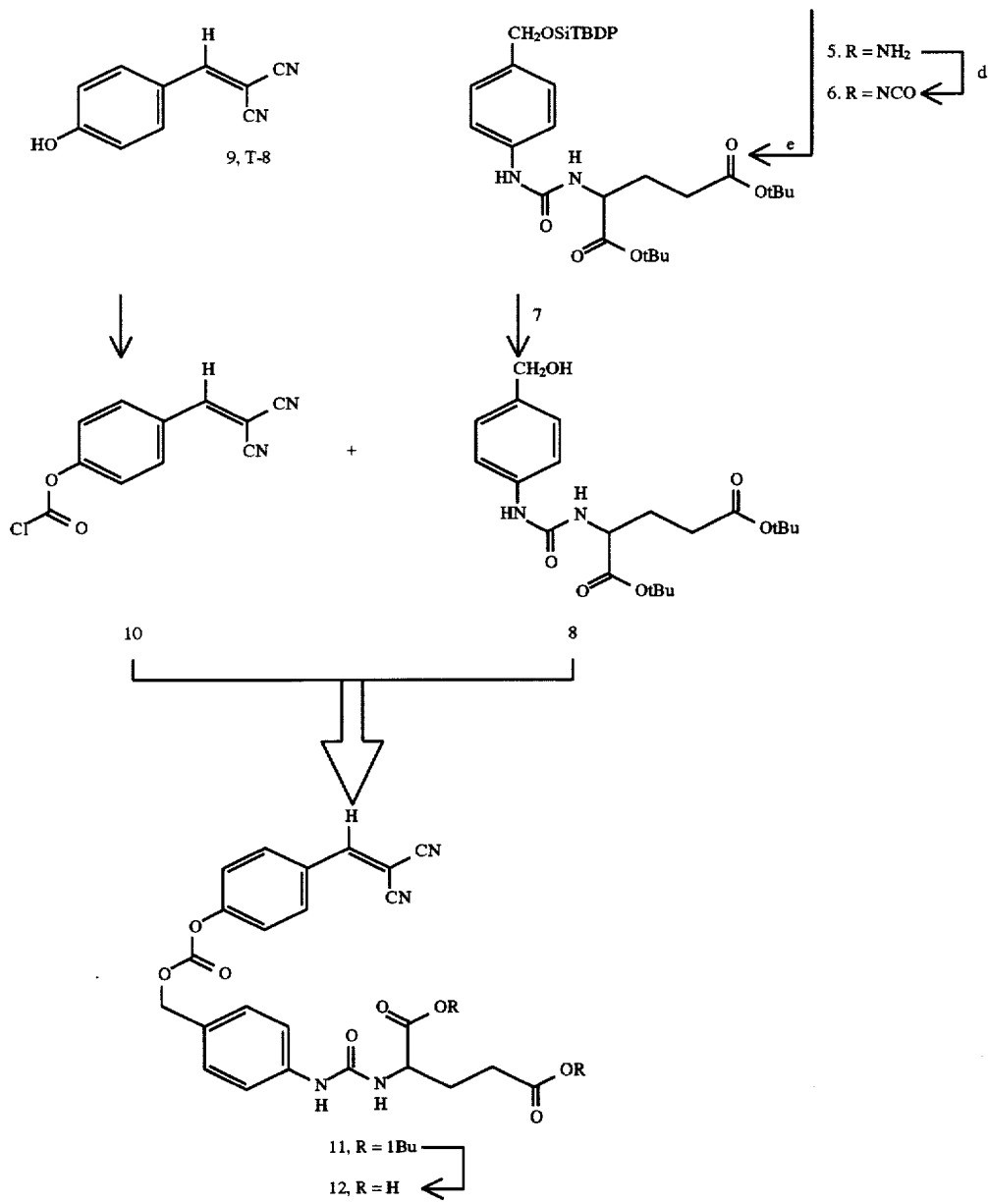
SCHEME 2
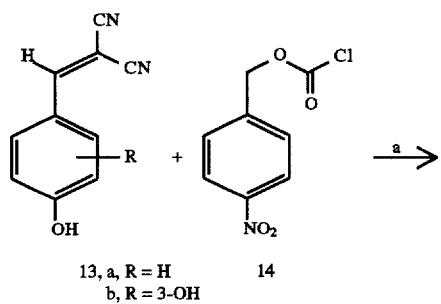

-continued
SCHEME 2

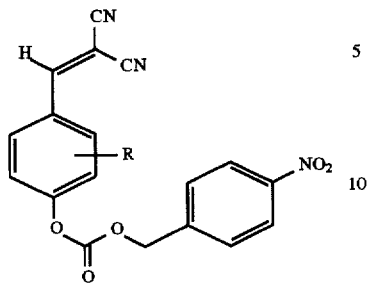

15, a, R = H
b, R = 3-OCOCH2C6H4NO2(p)

a: THF, NEt3, 20°.

SCHEME 3

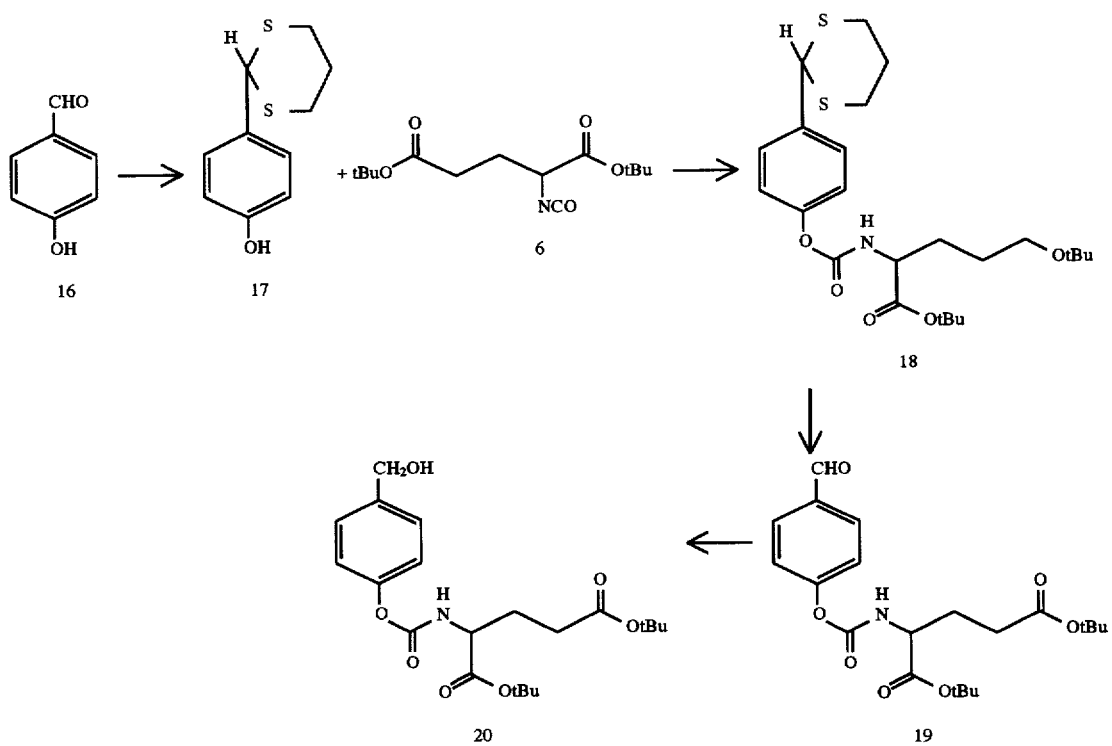

What is claimed is:

1. A compound of the formula (VII):

HOH2C—ph—NH—CO—NH—glu    (VII)

where Ph is an optionally substituted phenyl group and glu is the residue of glutamic acid of the formula:

—CH(CO2H)(CH2CH2CO2H)

or a di—$C_{1-6}$ alkyl ester thereof, and wherein the optionally substituted phenylene group is substituted at the 4-position by the glu-containing moiety relative to the hydroxymethyl group.

2. A compound of the formula (VIII):

HOH2C—Ph—O—CO—NH—glu    (VIII)

where Ph is an optionally substituted phenyl group and glu is the residue of glutamic acid of the formula:

—CH(CO2H)(CH2CH2CO2H)

or a di—$C_{1-6}$ alkyl ester thereof, and wherein the optionally substituted phenylene group is substituted at the 4-position by the glu-containing moiety relative to the hydroxymethyl group.

3. A compound selected from the group consisting of:
$N^1$(4-hydroxybenzyl)$N^3$(di-tert-butyl-glutamyl) urea; and
O(4-benzyl-oxy)N(di-tert-butyl-glutamyl) carbamate.

* * * * *